US012740956B2

(12) United States Patent
Iwasaki et al.

(10) Patent No.: US 12,740,956 B2
(45) Date of Patent: Sep. 22, 2026

(54) GABA-CONTAINING COMPOSITION

(71) Applicants: PHARMA FOODS INTERNATIONAL CO., LTD., Kyoto (JP); KYOTO PREFECTURAL PUBLIC UNIVERSITY CORPORATION, Kyoto (JP)

(72) Inventors: Yusaku Iwasaki, Kyoto (JP); Riho Sagane, Kyoto (JP); Utano Nakamura, Kyoto (JP); Maiko Miyazaki, Kyoto (JP); Atsushi Yamatsu, Kyoto (JP); Mujo Kim, Kyoto (JP)

(73) Assignees: PHARMA FOODS INTERNATIONAL CO., LTD., Kyoto (JP); KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 281 days.

(21) Appl. No.: 18/724,387

(22) PCT Filed: Dec. 28, 2022

(86) PCT No.: PCT/JP2022/048651

§ 371 (c)(1),
(2) Date: Jun. 26, 2024

(87) PCT Pub. No.: WO2023/127961

PCT Pub. Date: Jul. 6, 2023

(65) Prior Publication Data

US 2025/0221950 A1 Jul. 10, 2025

(30) Foreign Application Priority Data

Dec. 29, 2021 (JP) ................................ 2021-215421

(51) Int. Cl.
*A61K 31/197* (2006.01)
*A61P 3/04* (2006.01)

(52) U.S. Cl.
CPC .............. *A61K 31/197* (2013.01); *A61P 3/04* (2018.01)

(58) Field of Classification Search
None
See application file for complete search history.

(56) References Cited

U.S. PATENT DOCUMENTS

2010/0166675 A1 7/2010 Wang et al.

FOREIGN PATENT DOCUMENTS

| | | | |
|---|---|---|---|
| JP | 2006306851 | A | 11/2006 |
| JP | 200755951 | A | 3/2007 |
| JP | 2009201383 | A | 9/2009 |
| JP | 202097531 | A | 6/2020 |

OTHER PUBLICATIONS

Brubaker. Endocrinology, 1998, 139(10), 4108-4114 (Year: 1998).*
International Search Report for related International Application No. PCT/JP2022/048651 mailed Mar. 20, 2023 and its English Translation.
Sato, Kanako et al. Dietary GABA and its combination with vigabatrin mimic calorie restriction and induce antiobesity-like effects in lean mice. Journal of Functional Foods. Jan. 29, 2021. vol. 78. No. 104367, pp. 1-9.

* cited by examiner

*Primary Examiner* — Noble E Jarrell
(74) *Attorney, Agent, or Firm* — Renner, Otto, Boisselle & Sklar, LLP

(57) ABSTRACT

According to the present invention, a composition that induces the feeling of satiety or suppresses binge eating is provided. The present invention provides a GABA-containing composition for inducing transient satiety in a subject. The present invention also provides a GABA-containing composition for suppressing binge eating on a fasting condition in a subject.

19 Claims, 11 Drawing Sheets

[Fig. 1A]
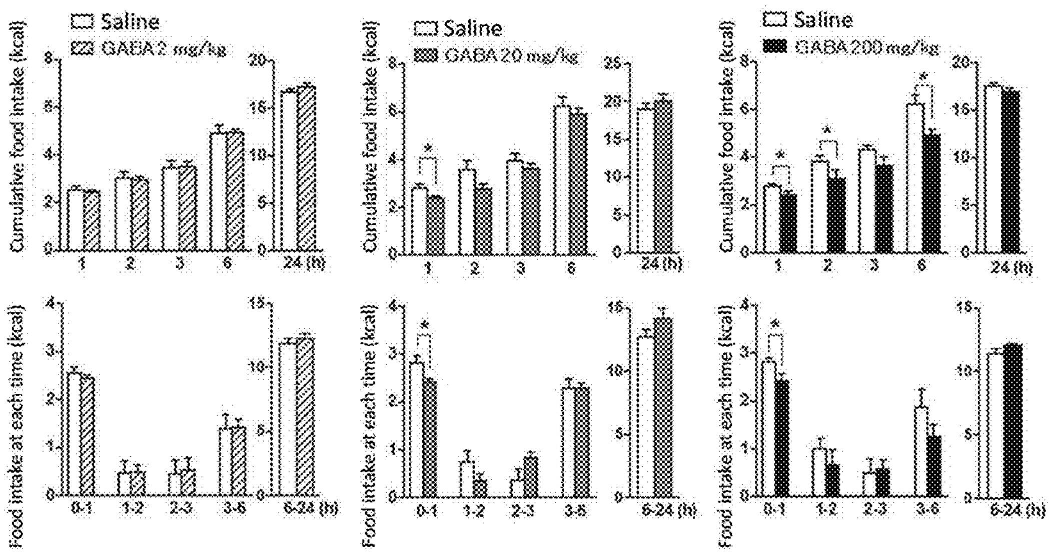
[Fig. 1B]
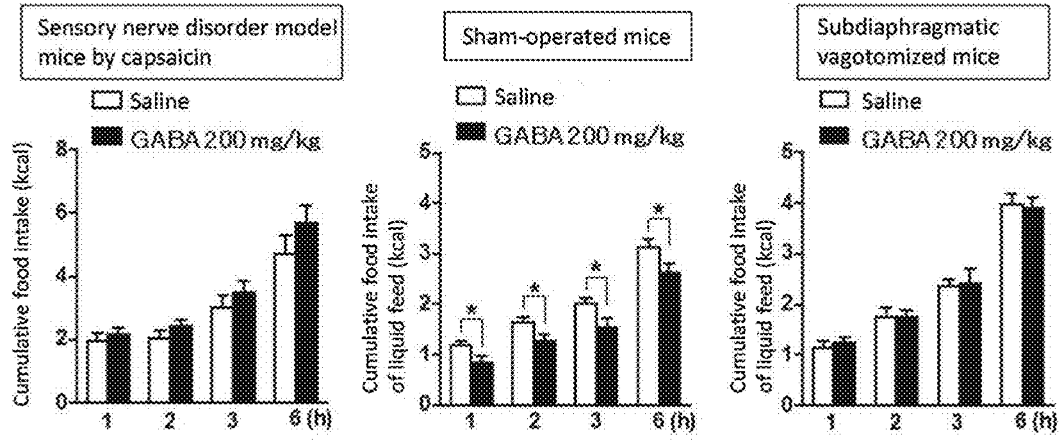

[Fig. 2]
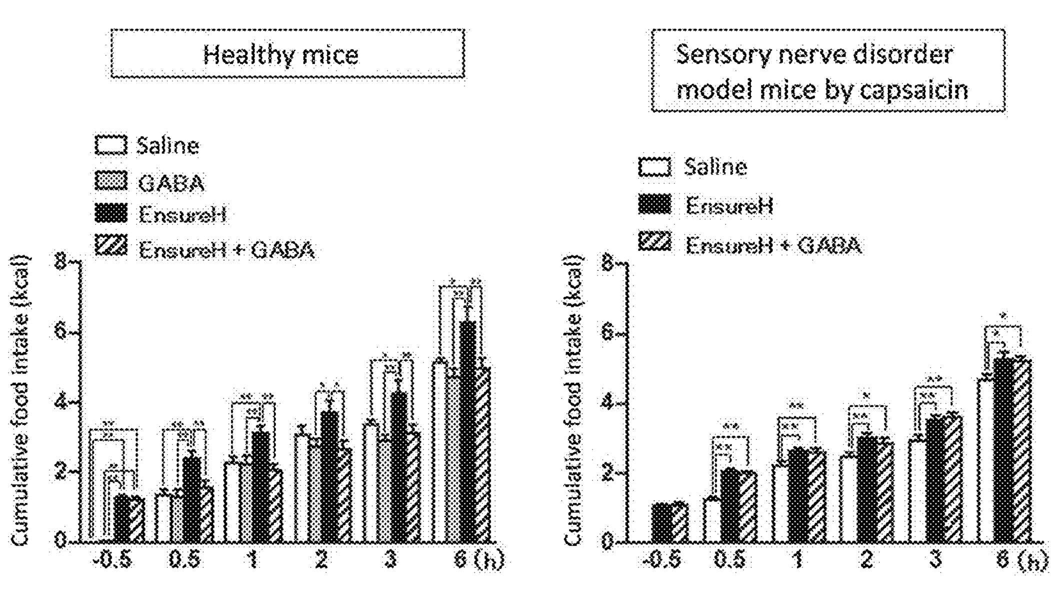
[Fig. 3]
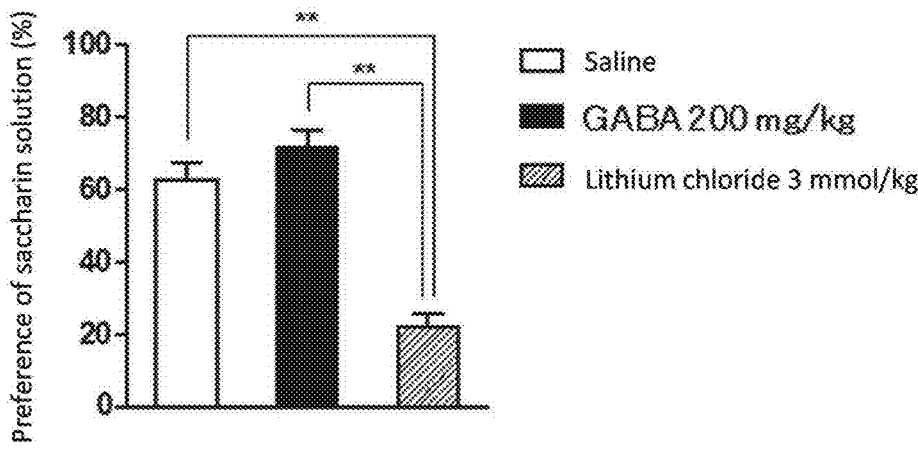

[Fig. 4]
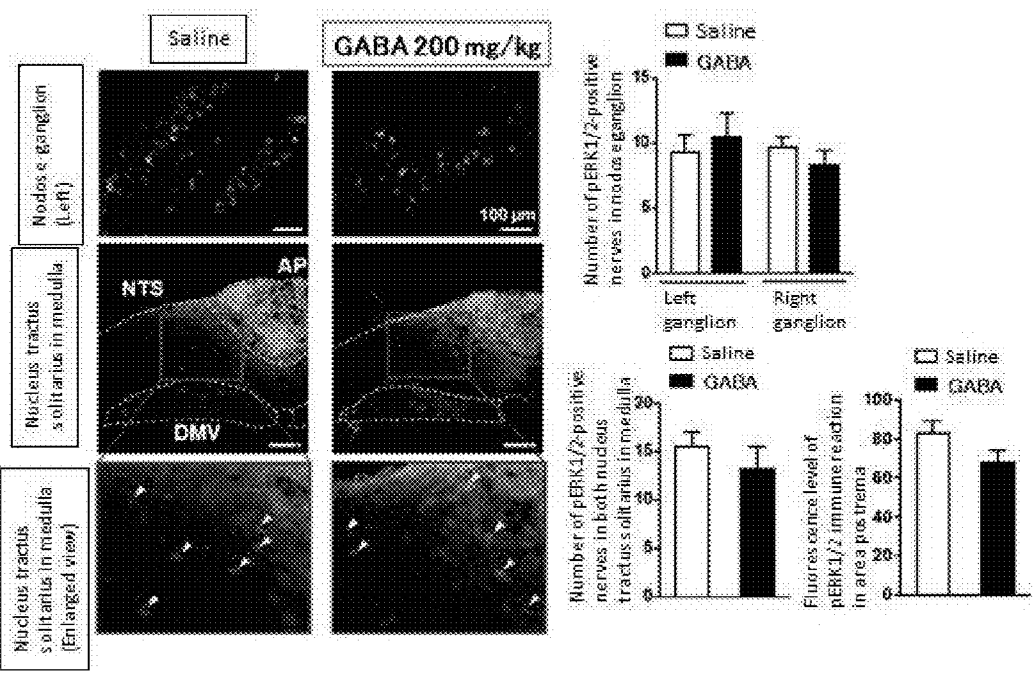
[Fig. 5A]
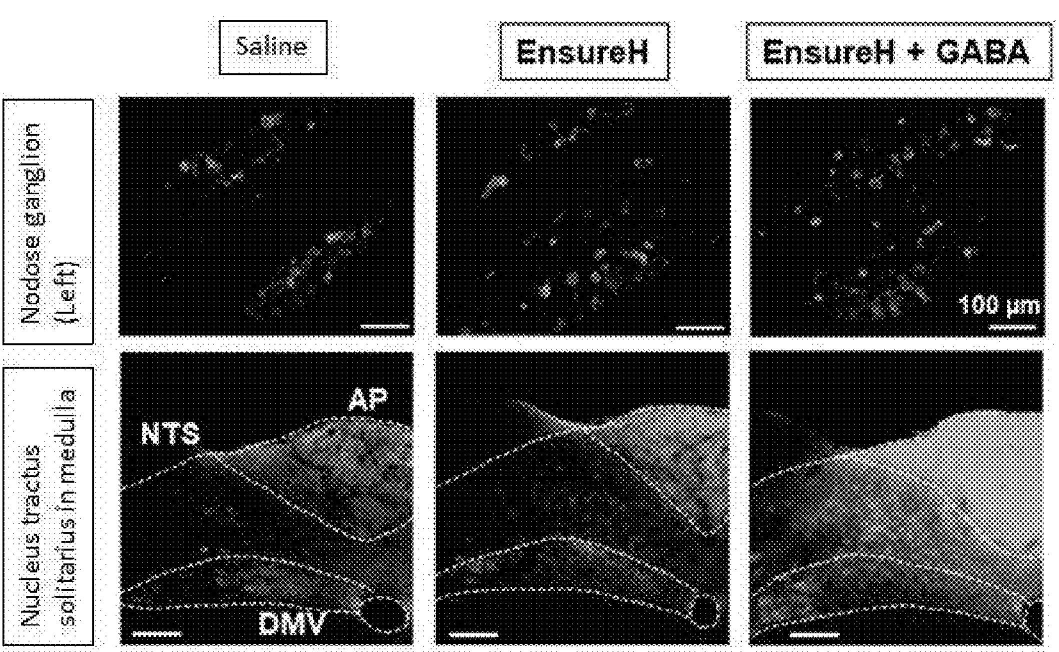

[Fig. 5B]
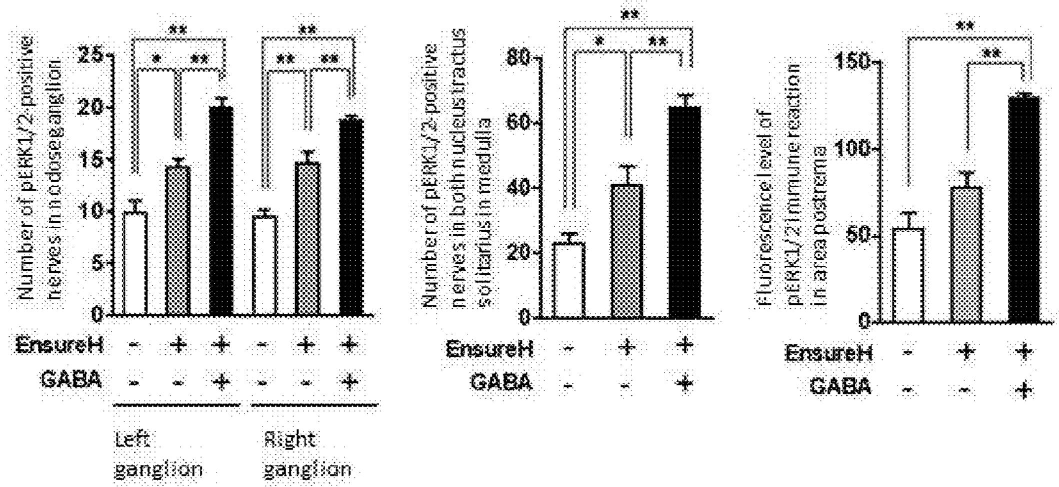
[Fig. 6]
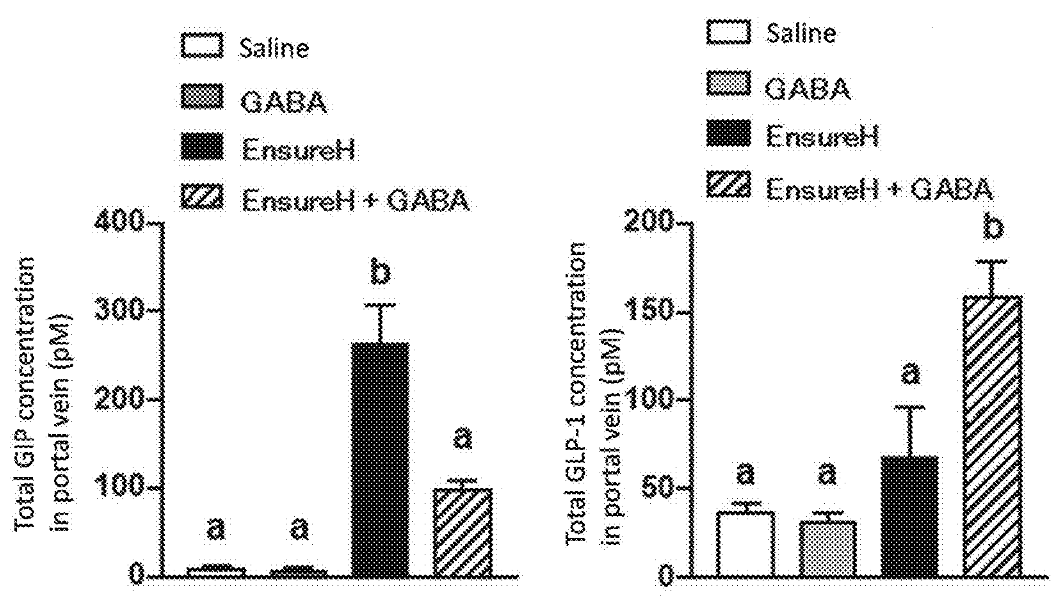

[Fig. 7]
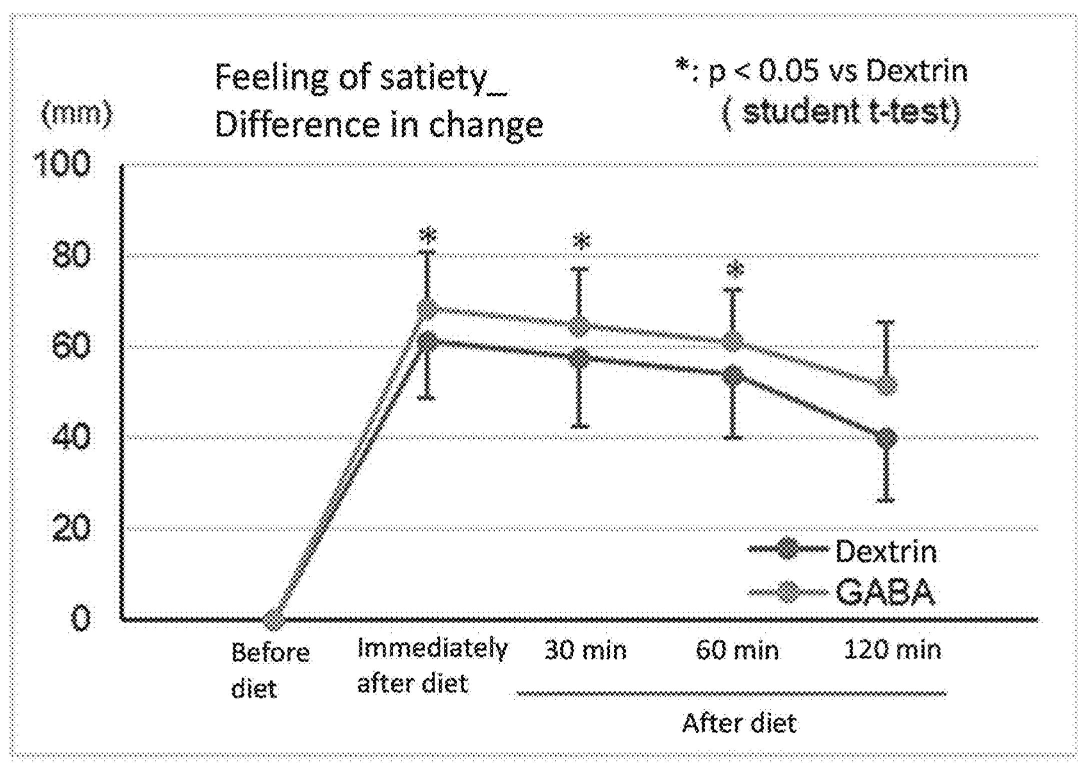
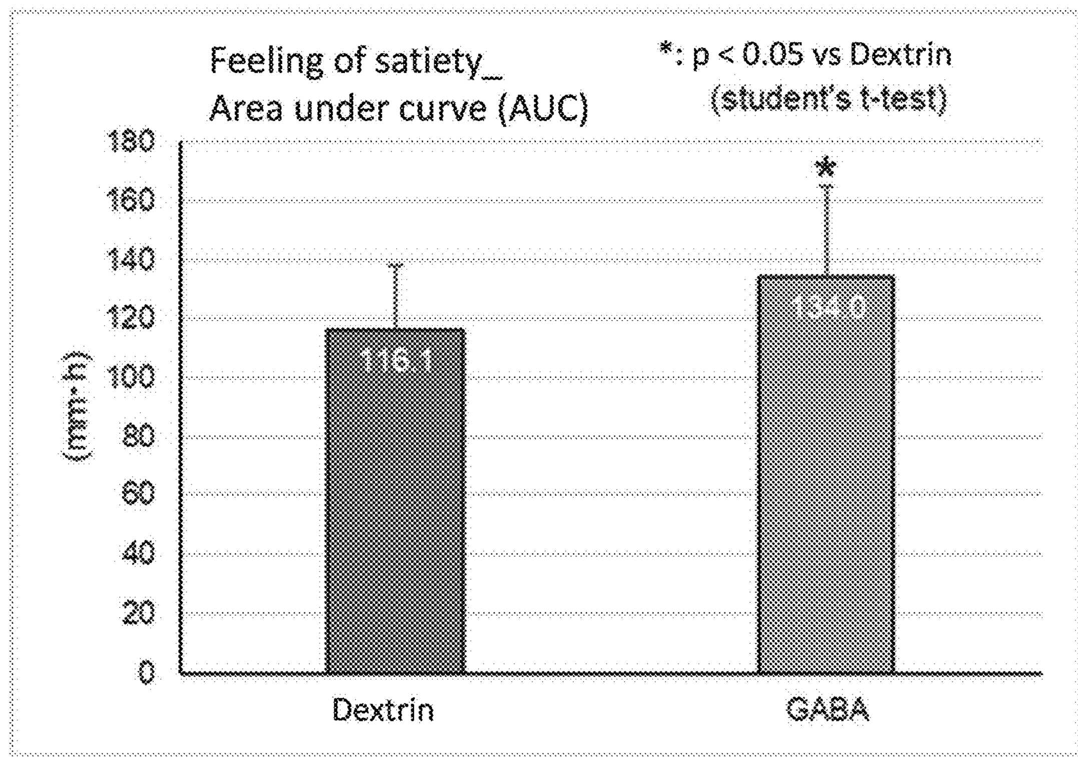

[Fig. 8]
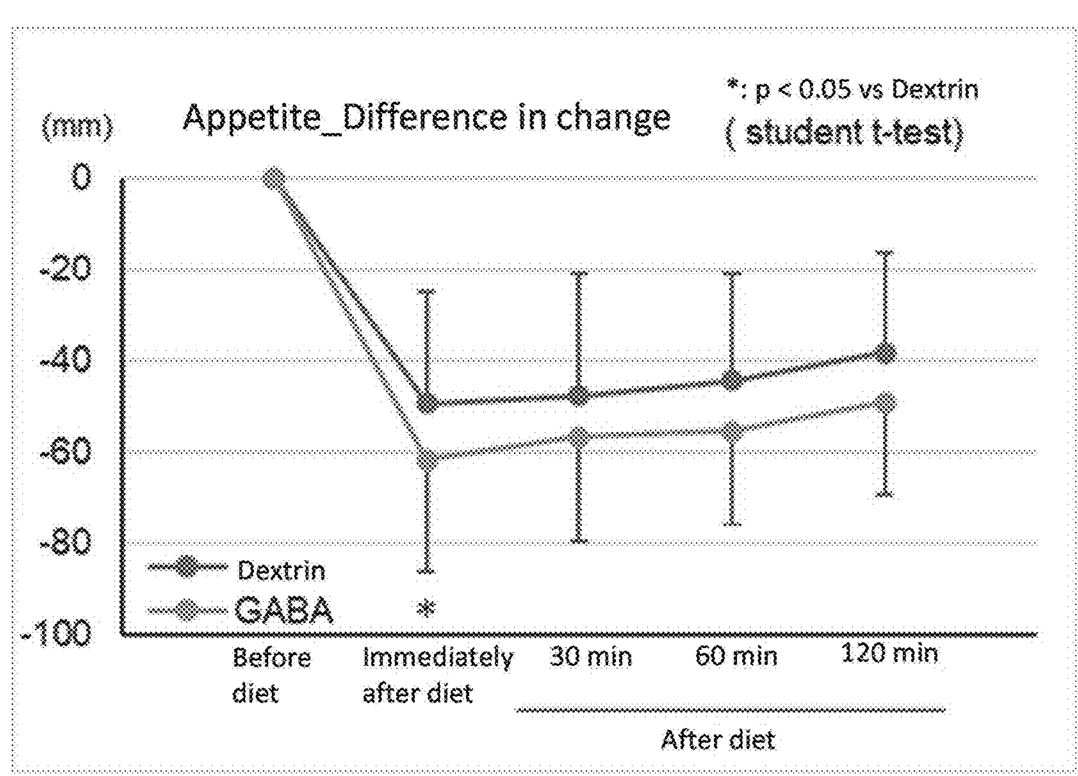

[Fig. 9]
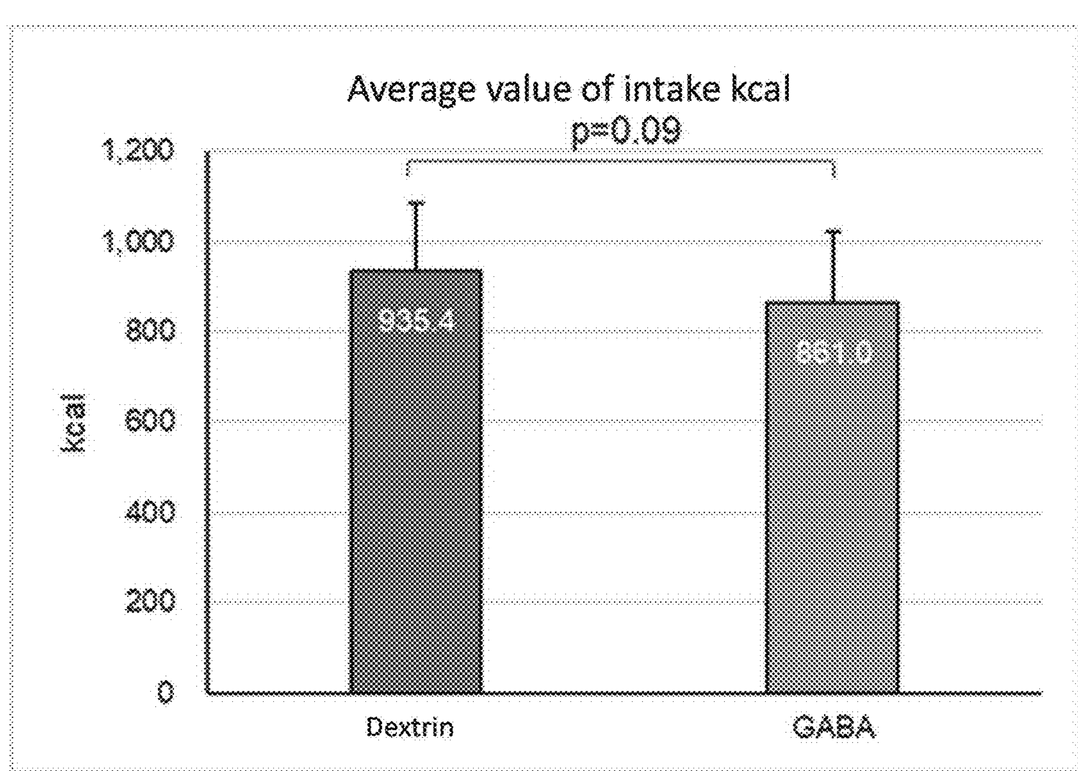

[Fig. 10]
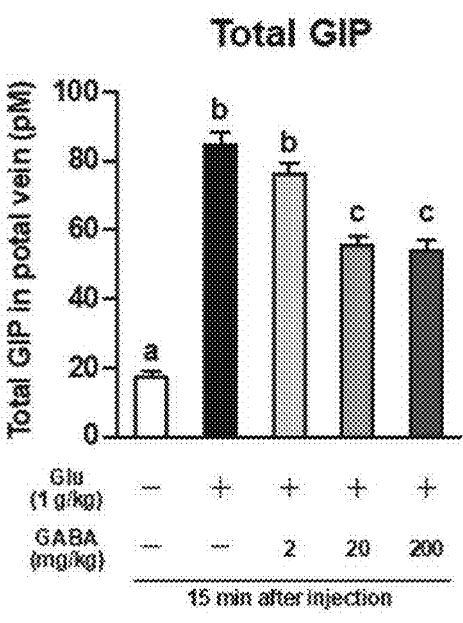
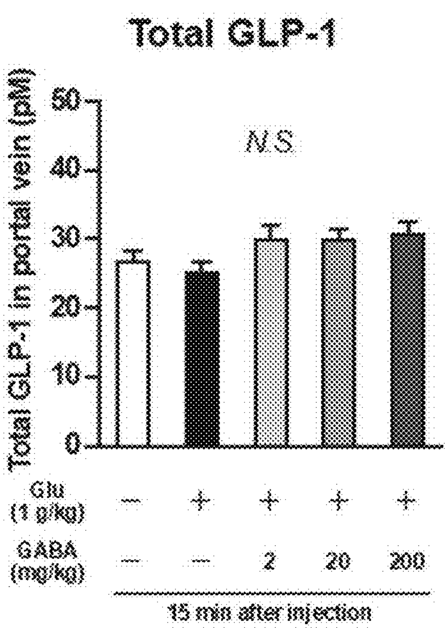
[Fig. 11]
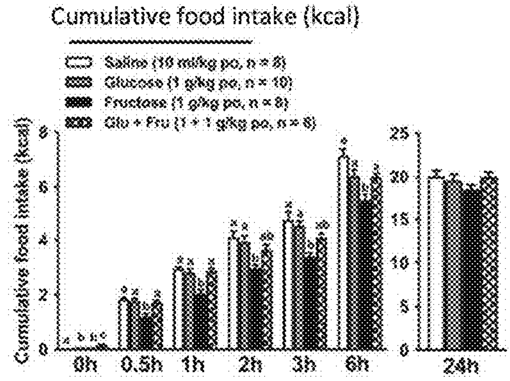
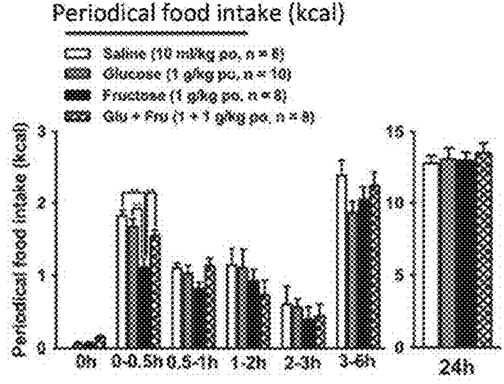

[Fig. 12]
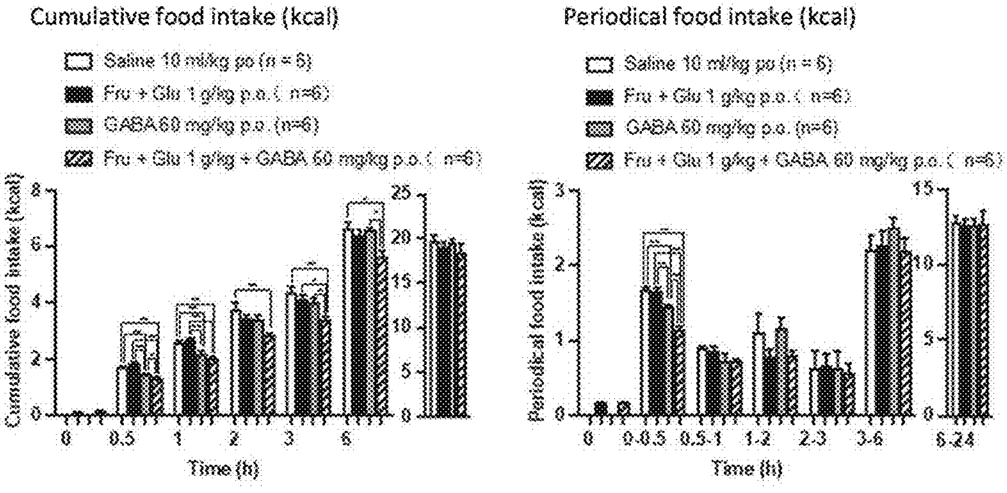

[Fig. 13]
GLP-1 Secretion
GIP Secretion
- Saline p.o. (n=5)
- Fructose 1 g/kg p.o. (n=5)
- Fru + Glu 1 g/kg p.o. (n=5)
- GABA 60 mg/kg p.o. (n=5)
- Fru + Glu 1 g/kg + GABA 60 mg/kg p.o. (n=5)
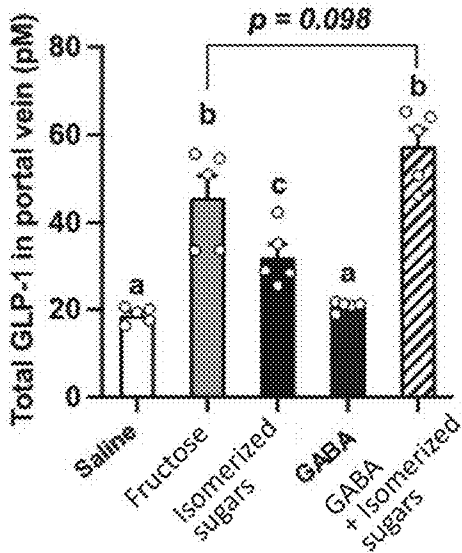
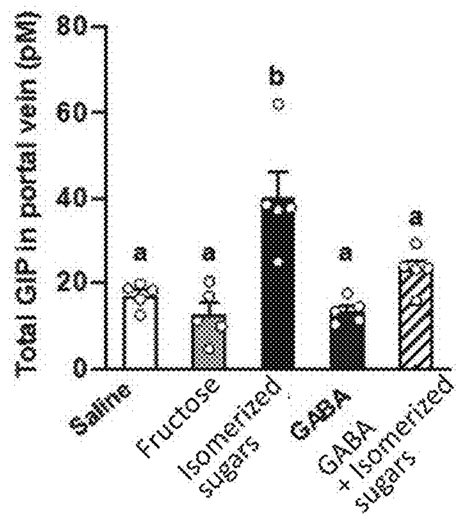

[Fig. 14]
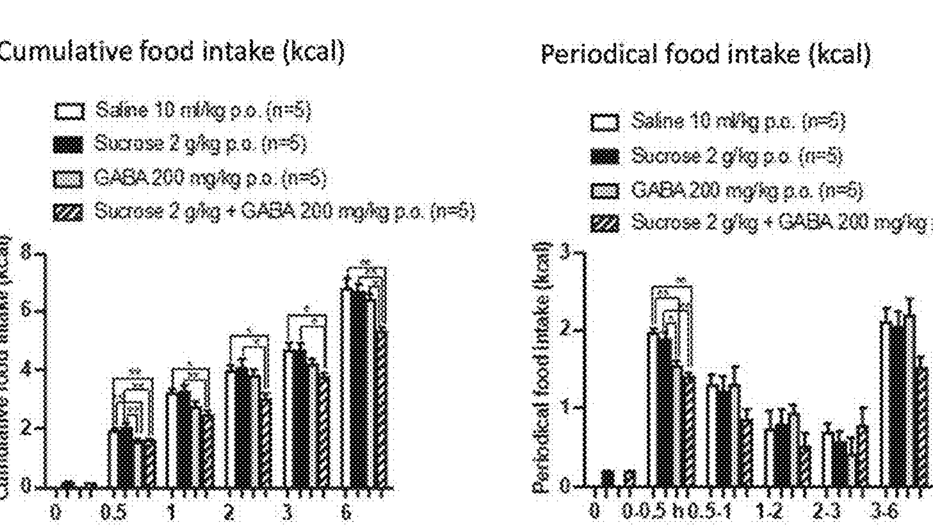

GABA-CONTAINING COMPOSITION

This application is a national phase of International Application No. PCT/JP2022/048651 filed 28 Dec. 2022, which claims priority to Japanese Application No. 2021-215421 filed 29 Dec. 2021, each of which is hereby incorporated herein by reference in its entirety.

TECHNICAL FIELD

The present invention relates to a GABA-containing composition for inducing transient satiety and/or suppressing binge eating.

BACKGROUND ART

In recent years, with the change in the way of life of modern people, the opportunity to take a high-fat diet has increased, and the lack of exercise has also progressed. In such a modern lifestyle, excessive caloric intake occurs, fat is accumulated, and a neutral fat level, a cholesterol level, a blood glucose level, or the like increases, and accordingly, obesity and metabolic syndrome become problems.

As obesity can cause various health disorders including various diseases, measures to prevent obesity are very important. In this regard, it is considered to be important to restrict the intake of diet and control the caloric intake in order to prevent obesity. However, it is necessary to have a strong will to voluntarily restrict the intake of diet, and it is difficult for many people to continuously restrict the intake of diet. In addition, the sense of hunger may cause a decrease in vitality and interfere with life. Therefore, there is a demand for a material that induces satiety or suppresses binge eating even when diet or calorie intake is restricted.

SUMMARY OF THE INVENTION

Problems to be Solved by the Invention

The present inventors have confirmed that γ-aminobutyric acid (GABA) has an effect of inducing transient satiety, and have further studied based on such findings, thereby finding that by using GABA, a composition for inducing transient satiety in a subject and/or suppressing binge eating on a fasting condition can be provided.

Therefore, according to a main aspect of the present invention, the following inventions are provided.

(Item 1)

A GABA-containing composition for inducing transient satiety in a subject.

(Item 2)

A GABA-containing composition for suppressing binge eating on a fasting condition in a subject.

(Item 3)

A GABA-containing composition for suppressing secretion of glucose-dependent insulinotropic polypeptide (GIP) in a subject.

(Item 4)

A GABA-containing composition for promoting secretion of glucagon-like peptide-1 (GLP-1) in a subject.

(Item 5)

The composition according to item 1 or 2, for achieving the induction or suppression by activating vagal afferent nerves.

(Item 6)

A GABA-containing composition for activating vagal afferent nerves in a subject.

(Item 7)

The composition according to any one of the preceding items, in which the composition is administered in combination with a component that activates vagal afferent nerves.

(Item 8)

The composition according to any one of the preceding items, in which the component that activates vagal afferent nerves is included in a diet.

(Item 9)

The composition according to any one of the preceding items, in which the component that activates vagal afferent nerves includes energy-producing nutrients, dietary fiber, polyphenols, sugar alcohols, and degradation products thereof.

(Item 9a)

The composition according to any one of the preceding items, in which the composition is administered in combination with glucose and sucrose.

(Item 10)

The composition according to any one of the preceding items, in which GABA is administered to the subject in an amount greater than or equal to about 100 mg/individual.

(Item 11)

The composition according to any one of the preceding items, in which GABA is administered to the subject in an amount greater than or equal to about 100 mg/individual once every about 3 hours or more.

(Item A1)

A method for inducing transient satiety in a subject, including administering a GABA-containing composition to the subject.

(Item A2)

A method for suppressing binge eating on a fasting condition in a subject, including administering a GABA-containing composition to the subject.

(Item A3)

A method for suppressing secretion of glucose-dependent insulinotropic polypeptide (GIP) in a subject, including administering a GABA-containing composition to the subject.

(Item A4)

A method for promoting secretion of glucagon-like peptide-1 (GLP-1) in a subject, including administering a GABA-containing composition to the subject.

(Item A5)

The method according to item A1 or A2, for achieving the induction or suppression by activating vagal afferent nerves.

(Item A6)

A method for activating vagal afferent nerves in a subject, including administering a GABA-containing composition to the subject.

(Item A7)

The method according to any one of the preceding items, in which the GABA-containing composition is administered in combination with a component that activates vagal afferent nerves.

(Item A8)

The method according to any one of the preceding items, in which the component that activates vagal afferent nerves is included in a diet.

(Item A9)

The method according to any one of the preceding items, in which the component that activates vagal afferent nerves includes energy-producing nutrients, dietary fiber, polyphenols, sugar alcohols, and degradation products thereof.

(Item A9a)

The method according to any one of the preceding items, in which the GABA-containing composition is administered in combination with glucose and sucrose.

(Item A10)

The method according to any one of the preceding items, in which GABA is administered to the subject in an amount greater than or equal to about 100 mg/individual.

(Item A11)

The method according to any one of the preceding items, in which GABA is administered to the subject in an amount greater than or equal to about 100 mg/individual once every about 3 hours or more.

In the present disclosure, it is intended that the one or more features may be provided in further combination in addition to the specified combination. Still further embodiments and advantages of the present disclosure will be appreciated by those skilled in the art upon reading and understanding the following detailed description if necessary.

Note that features and remarkable operations and effects of the present disclosure other than those described above will be apparent to those skilled in the art with reference to the following embodiments and drawings of the invention.

Advantages of the Invention

Since the GABA-containing composition of the present invention uses GABA, which is one of amino acids abundantly contained in vegetables, fruits, grains, or the like, it can be a highly safe composition. In addition, since GABA is generally a stable substance, it can be a composition that can be easily added to various foods.

Since the GABA-containing composition of the present invention can induce transient satiety and/or suppress binge eating, excessive caloric intake due to binge eating and drinking can be prevented. In addition, the GABA-containing composition of the present invention can prevent obesity due to excessive caloric intake, for example. Furthermore, the GABA-containing composition of the present invention can prevent health impairment due to, for example, obesity.

BRIEF DESCRIPTION OF THE DRAWINGS

FIG. 1A shows graphs according to an embodiment showing cumulative food intake (kcal) and food intake at each time (kcal) when GABA (2 mg/kg, 20 mg/kg, 200 mg/kg) was administered to healthy mice. It is shown that administration of the GABA solution just before feeding reduces subsequent food intake in the short term.

FIG. 1B shows graphs according to an embodiment showing cumulative food intake (kcal) when GABA (200 mg/kg) was administered to sensory nerve disorder model mice, sham-operated mice, or vagotomized mice.

FIG. 2 shows graphs according to an embodiment showing cumulative food intake (kcal) and food intake at each time (kcal) when GABA alone, an enteral nutrient alone, or a combination of GABA and an enteral nutrient was administered to healthy mice or sensory nerve disorder model mice 30 minutes before feeding. It is shown that GABA addition to enteral nutrients enhances satiety via vagal afferent nerves. On the other hand, in the administration of GABA 30 minutes before diet, the food intake reducing effect is greatly reduced, and thus it is shown that feeling of satiety is enhanced by taking GABA just before diet or together with diet.

FIG. 3 shows a result of a conditioned taste aversion test by GABA administration. That is, it is a graph according to an embodiment showing the preference of a saccharin solution when lithium chloride or GABA was administered to healthy mice (saccharin intake/total intake of two bottles×100, %). It is shown that lithium chloride inducing aversion has reduced preference of saccharin and induces aversion, but does not induce aversion even when GABA is administered.

FIG. 4 shows photographs and graphs according to an embodiment showing activity of nodose ganglion, or the nucleus tractus solitarius in the medulla and the area postrema, that are projection area of the vagal afferent nerves, when physiological saline or GABA was administered. It is shown that administration of GABA alone does not affect neuron activities of the vagal afferent nerves, the nucleus tractus solitarius in the medulla, or the area postrema.

FIG. 5A shows photographs according to an embodiment showing neuron activity of nodose ganglion, the nucleus tractus solitarius in the medulla (NTS), or the area postrema (AP) when only physiological saline, only an enteral nutrient, or a combination of an enteral nutrient and GABA was administered. It is shown that GABA addition to the diet enhances diet-induced nerve activation of the vagal afferent nerves, the nucleus tractus solitarius in the medulla, or the area postrema.

FIG. 5B shows graphs according to an embodiment showing neuron activity of nodose ganglion, the nucleus tractus solitarius in the medulla (NTS), or the area postrema (AP) when only physiological saline, only an enteral nutrient, or a combination of an enteral nutrient and GABA was administered. It is shown that GABA addition to the diet enhances diet-induced nerve activation of the vagal afferent nerves.

FIG. 6 shows graphs according to an embodiment showing the concentration of blood GIP or blood GLP-1 30 minutes after administration when only physiological saline, only GABA, only an enteral nutrient, or a combination of an enteral nutrient and GABA was administered. It is shown that GABA addition to enteral nutrients suppresses GIP secretion and promotes GLP-1 secretion.

FIG. 7 are graphs showing satiety enhancing action in humans by GABA intake. GABA intake significantly increased satiety immediately after diet, at 30 minutes and 60 minutes after diet, and GABA intake significantly increased satiety also in the area under the curve (AUC).

FIG. 8 is a graph showing an effect of suppressing binge eating in humans by GABA intake. GABA intake suppressed appetite after diet, indicating an effect of preventing binge eating.

FIG. 9 is a graph showing an effect of suppressing calorie intake in humans by GABA intake. It was shown that GABA intake provides satiety even with a small calorie intake.

FIG. 10 shows graphs showing an effect of suppressing glucose-induced GIP secretion by GABA intake.

FIG. 11 shows graphs showing an inhibitory effect of satiety inducing action of fructose by glucose.

FIG. 12 shows graphs showing an effect of GABA on an inhibitory action of fructose-induced satiety by glucose.

FIG. 13 is a graph showing an enhancing effect of fructose-induced GLP-1 secretion by GABA intake. Furthermore, FIG. 13 is a graph showing an effect of releasing the inhibitory action of glucose by GABA intake on the action of suppressing fructose-induced GLP-1 secretion by glucose.

FIG. 14 shows graphs showing an intake inhibitory action by intake of GABA and sucrose (sugar).

MODE FOR CARRYING OUT THE INVENTION

Hereinafter, the present disclosure will be described while showing the best mode. It should be understood that throughout the present specification, an expression in singular form also includes its concept in plural form, unless otherwise stated. Accordingly, it should be understood that a singular article (e.g., "a", "an", and "the" in English) also includes its concept in plural form, unless otherwise stated. In addition, it should also be understood that the terms used herein are used by the meanings which are commonly used in the art, unless otherwise stated. Accordingly, all technical terms and scientific terms used herein have the same meanings as those commonly understood by a person skilled in the art to which the present disclosure belongs, unless otherwise defined. In case of conflict, the present specification (including definitions) will control.

Hereinafter, definitions and/or basic technical contents of terms particularly used herein will be described as appropriate.

As used herein, "about" means±10% of the subsequent numerical value.

As used herein, "transient" refers to the occurrence of an event during a period of time within about 2 hours after administration of the composition to a subject, after which the event does not occur.

As used herein, "satiety" or "feeling of satiety" refers to the sensation or state of an individual, and refers to disappearance of the need for nutrition or the sense of hunger. The feeling of satiety can be obtained by a certain amount of diet. Because the feeling of satiety is a mental sensation, individuals who feel satisfied with the amount of diet tend to stop eating behavior, and thus satiety or the feeling of satiety can also be assessed by a decrease in food intake in the individual.

As used herein, "hungry" or "fasting condition" refers to the sensation or state of an individual, and refers to feeling the need for nutrition. Hungry is felt when there is little food in the stomach, such as between meals or during fasting, and is brought by fasting for about 3 hours or more.

The fasting blood glucose level in a normal human or animal is, for example, about 80 to about 100 mg/dL in the case of a human, whereas in the case of a diabetic patient or a candidate thereof, the fasting blood glucose level is, for example, about 126 mg/dL in the case of a human. Therefore, it is also possible to determine hungry according to the state of an individual.

As used herein, "binge eating" refers to a temporary feeling or condition of taking in more nutrients than an individual needs, and includes states such as eating a large amount of food, eating even when full, eating fast, or not being able to control eating behavior.

As used herein, "vagal afferent nerves" refers to a type of visceral sensory nerve that receives peripheral information, converts the peripheral information into neural information, and transmits the neural information to the nucleus tractus solitarius in the medulla and the area postrema. The "component that activates nerve activation of the vagal afferent nerves" is a component contained in food, and includes all components that can activate vagal afferent nerves. The "component that activates vagal afferent nerves" includes not only a component itself that serves as an energy source when taken and absorbed into the body, but also a substance that directly or indirectly assists energy production or is related to absorption or digestion of a certain component or nutrient even if the component itself does not serve as an energy source. Examples of the "component that activates vagal afferent nerves" include energy-producing nutrients (including proteins, lipids, and carbohydrates), dietary fibers, polyphenols, sugar alcohols, or degradation products thereof.

As used herein, the "energy-producing nutrient" refers to a component contained in food and can serve as an energy (calorie) source when taken and absorbed into the body, and specifically, it refers to a generic term for proteins, lipids, and carbohydrates. It can be used interchangeably with "three major nutrients".

Preferred Embodiments

Hereinafter, preferred embodiments of the present disclosure will be described. Embodiments described below are provided to facilitate the understanding of the present disclosure, and the scope of the present disclosure should not be limited to the following descriptions. Thus, it is apparent that those skilled in the art can make appropriate modifications within the scope of the present disclosure by referring to the descriptions herein. Also, the following embodiments of the present disclosure can be used alone or in combination.

γ-Aminobutyric acid (GABA, 4-aminobutyric acid) is widely distributed in nature, and has attracted attention in recent years as an amino acid that does not impair the taste thereof even when added to food. It is known that GABA is an inhibitory neurotransmitter that is abundantly present in the central nervous system of mammals, suppresses excessive secretion of excitatory neurotransmitters to suppress excitation of nerves, and exerts a relaxation effect and an anti-stress action. In addition, it is known to have a wide variety of physiological activities such as a blood pressure lowering action, a cholesterol lowering action, a stress alleviating action, a fatigue alleviating action, a sleep quality improving action, and suppression of reduction in immune strength. Since GABA is also contained in vegetables, grains, and human bodies, it is easily added to foods, and GABA-containing chocolate and many supplements are sold.

Since GABA is an amino acid widely distributed in nature, such as vegetables and grains, in one embodiment of the present invention, the origin and the like of GABA are not particularly limited as long as GABA can be used for food and drink. For example, an extract or a purified product of a plant containing GABA may be used, or it can also be prepared from a fermented product obtained by adding glutamic acid decarboxylase, microorganisms having the enzyme such as lactic acid bacterium or the like to a raw material containing glutamic acid. GABA-containing products and commercially available GABA can also be used as raw materials of the composition of the present invention as long as the effect of the composition of the present invention is not impaired.

In one embodiment of the present invention, when the composition of the present invention is for oral use, the form or dosage form thereof is not particularly limited, and a form suitable for oral intake can be appropriately selected according to the purpose. Specific examples thereof include forms such as powder (including granular), tablet, pill, powder, chewable, syrup, rod, plate, block, solid, solution, suspension, emulsion, granule, paste, cream, capsule such as hard capsule or soft capsule, suppository, injection, patch, and the like.

In one embodiment, the composition of the present invention may contain components other than GABA. For example, the composition of the present invention can contain additives necessary for formulation such as an excipient, a binder, a disintegrant, a lubricant, a stabilizer, a preservative, a flavoring agent, a pH adjusting agent, a colorant, and a diluent, which are usually added to food, and components that can be expected to have other functions as long as the effect of the composition of the present invention is not impaired. Also, in one embodiment of the present invention, the composition of the present invention can optionally contain components usually used in food production during production thereof. As the optional component, for example, proteins, carbohydrates, fats, nutrients, seasonings, flavors, and the like can be used. Examples of nutritionally acceptable additives include, but are not limited to, water, salt solutions, alcohols, silicones, waxes, petrolatum, vegetable oils, polyethylene glycols, propylene glycol, liposomes, sugars, gelatin, lactose, amylose, magnesium stearate, talc, surfactants, silicic acid, viscous paraffin, perfume oils, fatty acid monoglycerides and diglycerides, petroethral fatty acid esters, hydroxyl methyl cellulose, polyvinyl pyrrolidone, and the like.

The subject in the present invention is any mammal including livestock, pets, and the like, and is preferably a human.

In one embodiment, the method for administering the composition of the present invention is not particularly limited as long as it is commonly used, and may be either oral administration or parenteral administration. In addition, the dosage of the composition of the present invention is appropriately determined by those skilled in the art depending on the symptom, body weight, age, sex, and the like of the subject, but in a case where the subject is a human, in general, GABA in an amount of at least about 20 mg/body (individual), at least about 40 mg/body (individual), at least about 60 mg/body (individual), at least about 80 mg/body (individual), at least about 100 mg/body (individual), at least about 120 mg/body (individual), at least about 150 mg/body (individual), or at least about 200 mg/body (individual) as an active ingredient amount can be administered to the subject. In one embodiment, the total amount of the composition of the present invention per day may be any amount as long as the effect of the composition of the present invention can be obtained.

In one embodiment, the administration frequency of the composition of the present invention can be administered multiple times as long as the effect of the composition of the present invention is not impaired, and GABA can be administered to the subject at a timing of once about 1 hour or more, once about 2 hours or more, once about 3 hours or more, once about 4 hours or more, once about 5 hours or more, once about 7 hours or more, or once about 10 hours or more.

In one embodiment, the composition of the present invention can be administered in combination with food and drink including any food, drink, seasoning and the like, and the type of food and drink is not particularly limited. In addition, as long as the effect of the composition of the present invention is not impaired, any material usually contained in the food and drink can be appropriately blended in the food and drink. In one embodiment, the composition of the present invention can be administered in combination with the component that activates vagal afferent nerves, and the component is preferably included in a diet, such as food and drink. The component of the food and drink may be in the form of a liquid or a solid depending on the use or administration form. In one embodiment, examples of the component that activates vagal afferent nerves typically includes carbohydrates (including monosaccharides, disaccharides, trisaccharides, sugar alcohols, oligosaccharides and the like which can produce energy), proteins, lipids, dietary fibers (including water-soluble dietary fiber and insoluble dietary fiber), polyphenols, and caffeine, and degradation products thereof, and includes not only a component itself that serves as an energy source when taken and absorbed into the body, but also a substance that directly or indirectly assists energy production or is related to absorption or digestion of a certain component or nutrient even if the component itself does not serve as an energy source. The compositions of the present invention can be administered in combination with any food or drink or nutrient that can activate vagal afferent nerves.

Polyphenols are a general term for plant components having a plurality of phenolic hydroxy groups in the molecule, and as representative examples thereof, flavonoids, phenylpropanoids, hydrolyzed tannins, stilbenoids, and the like are exemplified, the flavonoids include non-polymer catechins, condensed tannins, theaflavins, quercetin, rutin, flavangenol, and pycnogenol, the phenylpropanoids include chlorogenic acid, caffeic acid, ferulic acid, and rosmarinic acid, the hydrolyzed tannins include tannic acid, pentagalloylglucose, gallic acid, ellagic acid, and ellagitannin, and the stilbenoids include resveratrol.

The "non-polymer catechins" are a generic term for non-epimeric catechins such as catechin, gallocatechin, catechin gallate, and gallocatechin gallate, and epimeric catechins such as epicatechin, epigallocatechin, epicatechin gallate, and epigallocatechin gallate. The "gallate forms of non-polymer catechins" are a generic term for catechin gallate, gallocatechin gallate, epicatechin gallate, epigallocatechin gallate, and the like.

The "chlorogenic acids" are a generic term for monocaffeoylquinic acids such as 3-caffeoylquinic acid, 4-caffeoylquinic acid, and 5-caffeoylquinic acid, monoferulicquinic acids such as 3-ferulicquinic acid, 4-ferulicquinic acid, and 5-ferulicquinic acid, and dicaffeoylquinic acids such as 3,4-dicaffeoylquinic acid, 3,5-dicaffeoylquinic acid, and 4,5-dicaffeoylquinic acid.

Examples of the sugar alcohol can include monosaccharide alcohols, disaccharide alcohols, and tri- or higher saccharide alcohols.

Examples of the monosaccharide alcohol include pentitols such as erythritol and xylitol, hexitols such as sorbitol and mannitol, and the like. Also, examples of the disaccharide alcohol include reduced maltose (maltitol), lactitol (reduced lactose), reduced palatinose (isomalt), trehalose, palatinose, and the like. Examples of the tri- or higher saccharide alcohol include maltotriitol, isomaltotriitol, panitol, and the like.

Examples of the caffeine include caffeine, anhydrous caffeine, sodium benzoate caffeine, and the like.

In one embodiment, the protein can include dietary proteins including, for example, animal proteins (milk proteins such as casein and whey, meat proteins, egg proteins, and the like), plant proteins (soybean proteins, wheat proteins, rice proteins, pea proteins, and the like), mixtures of free amino acids, amino acid (BCAA and the like) supplements or formulations, or combinations thereof. The protein may be untreated or hydrolyzed or may be a mixture of untreated and hydrolyzed proteins.

In one embodiment, the lipid includes simple lipids (neutral fat, wax, and the like), complex lipids (phospholipids, glycolipids, lipoproteins, and the like), and induced lipids (sterols and the like), and can include, for example, unsaturated fatty acids including monounsaturated fatty acids and polyunsaturated fatty acids, and fatty acids included in foods such as saturated fatty acids. The fatty acid can include butyric acid, octanoic acid, palmitic acid, stearic acid, oleic acid, DHA, EPA, α-linolenic acid, linoleic acid, arachidonic acid, or combinations thereof.

In one embodiment, examples of the carbohydrate can include sucrose, lactose, glucose, fructose, corn syrup (isomerized sugar), maltodextrin, starch, sorbitol, xylitol, maltitol, lactitol, mannitol, erythritol, and mixtures thereof.

In one embodiment of the present invention, the composition of the present invention can be administered in combination with these nutrients or diets, and preferably can be administered about 30 minutes, about 25 minutes, about 20 minutes, about 15 minutes, about 10 minutes, about 5 minutes before intake of nutrients or diets. In another embodiment, the composition of the present invention can be administered within about 60 minutes, within about 30 minutes, within about 25 minutes, within about 20 minutes, within about 15 minutes, within about 10 minutes, within about 5 minutes after intake of nutrients or diets. In one embodiment, the composition of the present invention can also be taken with nutrients or diets.

Thus, in one embodiment of the present invention, the composition of the present invention, when administered to a human, for example, can be administered to a fasting subject in an amount of at least about 100 mg/body, which can be administered in combination with proteins, carbohydrates, lipids, vitamins, and/or minerals, and the like, and can be administered in one timing over about 3 hours or more.

In one embodiment, the subject for use or administration of the composition of the present invention is not particularly limited, and examples thereof include humans such as babies, infants, children, juveniles, and adults. The subject for use or administration of the composition of the present invention may be mammals such as cats, dogs, guinea pigs, rabbits, pigs, cows, horses, sheep, goats, or poultry. In one embodiment, the body weight and the numerical value of body of the subject for use or administration of the composition of the present invention are not particularly limited, and any subject can be applied.

(Transient Satiety-Inducing Ability/Binge Eating Suppressing Ability)

In an aspect of the present invention, a GABA-containing composition for inducing transient satiety in a subject is provided. In another aspect of the present invention, a GABA-containing composition for suppressing binge eating on a fasting condition in a subject is provided.

In one embodiment, the composition of the present invention can induce transient satiety in a subject and/or suppress binge eating on a fasting condition. In one embodiment, the composition of the present invention can induce the feeling of satiety in a subject within about 2 hours, within about 90 minutes, within about 60 hours, within about 45 minutes, within about 30 minutes, or within about 15 minutes after administration, whereby the subject can suppress intake of more food than the subject requires. In one embodiment, the composition of the present invention is preferably administered within about 30 minutes after intake of diet, which activates vagal afferent nerves, induces the feeling of satiety, and/or attenuates the sense of hunger.

(Function of Activating Vagal Afferent Nerves)

In an aspect of the present disclosure, a GABA-containing composition for activating vagal afferent nerves in a subject is provided.

The vagal afferent nerves is a type of visceral sensory nerve that receives peripheral information, converts the peripheral information into neural information, and transmits the neural information to the nucleus tractus solitarius in the medulla, and it is known that a food-related hormone (gastrointestinal pancreatic hormone) whose secretion is interlocked before and after diet directly acts on the vagal afferent nerves to adjust the food intake. For example, in GLP-1, a pathway via an autonomic afferent pathway called a neural pathway is known, and a stimulus is transmitted to the nucleus tractus solitarius in the medulla and the hypothalamus in the brain via vagal afferent nerves or an afferent sympathetic nerve from the gastrointestinal tract.

Regarding the relationship between the vagus nerve and GLP-1 and GIP, it is known that when the receptor gene expression of GLP-1 and GIP in the ganglion is confirmed, the gene expression of GLP-1 receptor is confirmed, whereas the receptor gene expression of GIP cannot be substantially confirmed (Auton Neurosci. 2004 Jan. 30; 110(1): 36-43). It is also known that when whether GLP-1 and GIP affect the vagus nerve is examined, administration of GLP-1 into the hepatic portal vein leads to a significant increase in neural activity of afferent nerves in the hepatic branch of the vagus nerve, whereas administration of GIP does not result in any change in afferent vagal activity (J Auton Nerv Syst. 1996 Nov. 6; 61(2): 149-54). From the above, without being bound by theory, it can be said that GLP-1 activates the vagus nerve and GIP does not affect vagal activity.

Without intending to be bound by theory, the composition of the present invention can induce transient satiety and/or suppress binge eating on a fasting condition by activating vagal afferent nerves.

In one embodiment, the composition of the present invention can ameliorate, treat, or prevent a disease by activating vagal afferent nerves, and the target disease may be a disease whose symptoms are ameliorated, treated, or prevented by stimulation of the vagus nerve, and examples thereof include drug resistant epilepsy, treatment resistant depression, migraine/cluster headache, stroke, inflammation, involuntary movement, obesity/binge eating, Alzheimer's disease, and/or the like.

In one embodiment, the composition of the present invention may enhance afferent vagal activation by any food or drink or nutrient that may activate vagal afferent nerves. Nutrients that may activate vagal afferent nerves may be proteins, carbohydrates, and/or lipids, as described above, and these nutrients are preferably included in a diet, such as food and drink. The component of the food and drink may be in the form of a liquid or a solid depending on the use or administration form.

(GLP-1 Secretion-Promoting Function)

In an aspect of the present disclosure, there is provided a GABA-containing composition for promoting secretion of glucagon-like peptide-1 (GLP-1) in a subject.

GLP-1 (Glucagon-like peptide-1) is an endocrine physiologically active substance produced in endocrine cells (L cells). L cells are present in the mucosal epithelium of the gastrointestinal tract from the ileum to the colon. GLP-1 is a type of hormone called incretin (Intestine Secretion Insulin), which is secreted from the gastrointestinal tract along with intake of nutrients and acts on pancreatic β cells to promote insulin secretion. GLP-1 is known to have various physiological activities via signaling caused by binding to GLP-1 receptor.

GLP-1 exhibits a function improving action on the central nervous system such as suppression of gastric acid secretion and suppression of appetite and eating through binding to GLP-1 receptor present in the central nervous system. In addition, GLP-1 promotes uptake of sugar into muscle through the promotion of insulin secretion, and promotes growth and proliferation of muscle cells. GLP-1 can also provide a thrombogenesis inhibitory action and an arteriosclerosis improving action by promoting production of nitric oxide (NO) from vascular endothelial cells via the GLP-1 receptor.

In one embodiment, the composition of the present invention can promote secretion of endogenous GLP-1 and increase the in vivo GLP-1 concentration. This can induce physiological activities by GLP-1, such as suppression of appetite and eating, promotion of sugar uptake into muscles, suppression of thrombogenesis, improvement of arteriosclerosis, reduction of systolic blood pressure, and improvement of central nervous system function. The composition of the present invention can also promote the secretion of GLP-1, thereby suppressing binge eating or inducing the feeling of satiety.

In one embodiment, the composition of the present invention can promote an increase in blood GLP-1 concentration associated with GLP-1 secretion in vivo, maintain the increased GLP-1 concentration, or suppress a decrease in the increased GLP-1 concentration. In one embodiment, the promotion of GLP-1 secretion can include an increase in the blood GLP-1 level by orally taking the composition of the present invention. There is also a phenomenon in which GLP-1 secretion in vivo caused by diet is promoted by intake of the composition of the present invention.

In one embodiment, the GLP-1 secretion promoting action of the composition of the present invention should be such that the in vivo GLP-1 concentration when the composition of the present invention is used is higher than the in vivo GLP-1 concentration when the composition of the present invention is not used, and is, for example, about 1.1 times or more, preferably about 1.2 times or more, and more preferably about 1.3 times or more the in vivo GLP-1 concentration when the composition of the present invention is not used. The composition of the present invention can be utilized in various forms with the aim of obtaining a GLP-1 secretion promoting action. For example, the composition of the present invention may be used for various purposes without adding special processing.

(GIP Secretion Inhibitory Function)

In an aspect of the present disclosure, there is provided a GABA-containing composition for suppressing secretion of glucose-dependent insulinotropic polypeptide (GIP) in a subject.

Glucose-dependent insulinotropic polypeptide (GIP) is a peptide called incretin like GLP-1, and is secreted into the blood from L cells and K cells of the small intestine in response to oral nutrition intake. GIP is known to inhibit gastric acid secretion and to be a potent stimulator of insulin secretion from pancreatic R cells after oral glucose intake.

In one embodiment of the present invention, the composition of the present invention can suppress GIP secretion and reduce the in vivo GIP concentration. Thereby, for example, inhibition of gastric acid secretion is suppressed, and a decrease in insulin secretion can be induced.

In one embodiment, the composition of the present invention can suppress a blood GIP concentration associated with GIP secretion inhibition in vivo, maintain the reduced GIP concentration, or suppress an increase in the reduced GIP concentration. In one embodiment, the GIP secretion inhibition can include a reduction in the blood GIP level by orally taking the composition of the present invention. There is also a phenomenon in which GIP secretion in vivo caused by diet is suppressed by intake of the composition of the present invention.

In one embodiment, the GIP secretion inhibitory action of the composition of the present invention should be such that the in vivo GIP concentration when the composition of the present invention is used is lower than the in vivo GIP concentration when the composition of the present invention is not used, and is, for example, about 0.9 times or less, preferably about 0.8 times or less, and more preferably about 0.7 times or less the in vivo GIP concentration when the composition of the present invention is not used. The composition of the present invention can be utilized in various forms with the aim of obtaining a GIP secretion inhibitory action. For example, the composition of the present invention may be used for various purposes without adding special processing.

Adipocytes are known to secrete leptin, a potent intake inhibitor, and in normal states, leptin functions to prevent overeating. However, in the early stage of obesity, leptin resistance in which the action of leptin is attenuated is developed, satiety effect by leptin is attenuated, and binge eating occurs. GIP is known as a molecule involved in the onset of leptin resistance (Kaneko K et al. J Clin Invest 2019, PMID: 31403469), and in one embodiment, the composition of the present invention can induce the feeling of satiety through the GIP secretion inhibitory action.

Fat accumulation (obesity) itself is also considered as one cause of leptin resistance, and eating a high-fat diet leads to binge eating and obesity. It is known that a mouse deficient in the GIP receptor does not become obese even when fed a high-fat diet (Miyawaki K. et al. Nat Med 2002, PMID: 12068290), and in one embodiment, the composition of the present invention can suppress obesity through the GIP secretion inhibitory action.

In addition, in human studies, it is known that the energy intake can be reduced by intravenously administering GLP-1 to obese patients, but the effect of GLP-1 is attenuated by simultaneously administering GIP (Bergmann N. C. et al. Diabetologia 2019, PMID: 30683945). Therefore, in one embodiment, the composition of the present invention can also enhance the energy intake reducing action of GLP-1 through the GIP secretion inhibitory action.

(Effect of GABA Intake on Intake of Glucose, Sucrose, and/or Isomerized Sugar)

In one embodiment, the GABA-containing composition of the present invention can suppress glucose-induced GIP secretion. Intake of glucose increases GIP secretion, but the GABA-containing composition of the present invention can suppress such an increase in GIP secretion by glucose.

In one embodiment, the GABA-containing composition of the present invention can release the inhibitory effect on the intake inhibitory action of fructose by glucose. When fructose is taken alone, the feeling of satiety can be induced, but when glucose is further taken in addition to fructose, glucose inhibits the satiety inducing action by fructose, and the feeling of satiety induced by fructose is suppressed. The GABA-containing composition of the present invention can release such an inhibitory effect on the intake inhibitory action of fructose by glucose. The combination of glucose and fructose may be taken as an isomerized sugar. As used herein, the "isomerized sugar" refers to a sugar containing glucose and fructose as main components, and can contain glucose and fructose at a ratio of about 1:about 9 to about 9:about 1 (weight ratio).

Also in one embodiment, the GABA-containing composition of the present invention can enhance fructose-induced GLP-1 secretion. Intake of fructose increases GLP-1 secretion, but the GABA-containing composition of the present invention can further enhance such GLP-1 secretion by fructose. In one embodiment, GABA, fructose, and glucose can be taken in a ratio (weight ratio) of GABA fructose glucose=about 0.01:about 1:about 1 to about 1 about 1:about 1, and fructose-induced GLP-1 secretion can be enhanced by taking preferably in a ratio (weight ratio) of GABA:fructose: glucose=about 0.06:about 1:about 1. In another embodiment, fructose-induced GLP-1 secretion can also be enhanced when the amount of GABA is greater than the amount of fructose or glucose, and fructose-induced GLP-1 secretion can be enhanced by taking, for example, GABA, fructose, and glucose in a ratio (weight ratio) of GABA: fructose:glucose=about 1:about 1:about 1 to about 10:about 1:about 1. In another embodiment, fructose-induced GLP-1 secretion can also be enhanced when the ratio of fructose and glucose is changed. For example, fructose-induced GLP-1 secretion can be enhanced by taking a GABA-containing composition containing fructose:glucose at a ratio (by weight ratio) of about 1:about 10 to about 10:about 1 and GABA at a ratio (by weight) of about 0.1 to about 10 times the total amount of fructose and glucose.

In yet another embodiment, the GABA-containing composition of the present invention can suppress isomerized sugar-induced GIP secretion. Although intake of isomerized sugar increases GIP secretion, the GABA-containing composition of the present invention can suppress such an increase in GIP secretion by isomerized sugar. In one embodiment, GABA, fructose, and glucose can be taken in a ratio (weight ratio) of GABA:fructose:glucose=about 0.01: about 1:about 1 to about 1:about 1:about 1, and the increase in GIP secretion by isomerized sugar can be suppressed by taking preferably in a ratio (weight ratio) of GABA:fructose: glucose=about 0.06:about 1:about 1. In another embodiment, the increase in GIP secretion by isomerized sugar can also be suppressed when the amount of GABA is greater than the amount of fructose or glucose, and the increase in GIP secretion by isomerized sugar can be suppressed by taking, for example, GABA, fructose, and glucose in a ratio (weight ratio) of GABA:fructose:glucose=about 1:about 1 about 1 to about 10:about 1:about 1. In another embodiment, the increase in GIP secretion by isomerized sugar can also be suppressed when the ratio of fructose and glucose is changed. For example, the increase in GIP secretion by isomerized sugar can be suppressed by taking a GABA-containing composition containing fructose:glucose at a ratio (weight ratio) of about 1:about 10 to about 10:about 1 and GABA at a ratio (weight ratio) of about 0.1 times to about 10 times the total amount of fructose and glucose.

Also in one embodiment, the GABA-containing composition of the present invention can induce the feeling of satiety and/or suppress food intake by being taken in combination with sucrose (sugar). When sucrose (sugar) is taken alone, the satiety inducing action (intake inhibitory action) is not observed, but the feeling of satiety can be induced and/or the food intake can be suppressed by taking the GABA-containing composition of the present invention together with sucrose (sugar, disaccharide composed of glucose and fructose). In one embodiment, GABA and sucrose can be taken in a ratio (by weight) of GABA: sucrose=about 1:about 1 to about 1:about 100, and the feeling of satiety can be induced and/or the food intake can be suppressed by taking preferably in a ratio (weight ratio) of GABA:sucrose=about 1:about 10. In another embodiment, the feeling of satiety can be also induced and/or food intake can be also suppressed when the amount of GABA is greater than the amount of sucrose, and the feeling of satiety can be induced and/or the food intake can be suppressed by taking, for example, in a ratio (weight ratio) of GABA: sucrose=about 100:about 1 to about 1:about 1.

As used herein, "or" is used when "at least one or more" of the listed matters in the sentence can be employed. The same applies to "or". When explicitly described herein as "within the range" of "two values", the range also includes the two values themselves.

Reference literatures such as scientific literatures, patents, and patent applications cited herein are incorporated herein by reference to the same extent that the entirety of each document is specifically described.

As described above, the present disclosure has been described while showing preferred embodiments to facilitate understanding. Hereinafter, the present disclosure will be described based on Examples, but the aforementioned description and the following Examples are not provided to limit the present disclosure, but for the sole purpose of exemplification. Accordingly, the scope of the present disclosure is not limited by the embodiments and the examples that are specifically described herein, and is limited only by the claims.

EXAMPLES

Example 1: Effect of GABA Administration on Food Intake

As experimental animals, C57BL/6J male mice were used. The mice were acclimated to the environment by preliminary rearing for 1 week or more in individual cages in the free-eating and drinking environment at a temperature of 23±2° C., a humidity of 55±10%, a 12 hour light-dark cycle (light period: 7:30 to 19:30). The animal experiment was conducted with approval in accordance with the guidelines of the Committee for Animal Research of Kyoto Prefectural University.

Healthy C57BL/6J male mice were fasted for 16 hours from 18:00 on the day before the experiment. In each administration, the mice were intragastrically administered (po) a single dose of physiological saline as a control group and GABA (2 mg/kg, 20 mg/kg, 200 mg/kg) as a test group at a dose of 10 ml/kg using a sonde (stainless steel feeding needle). Each solution was administered from 9:45, and the mice were freely fed CE-2 feed (a standard mouse feed with a good nutritional balance, 3.4 kcal/kg, manufactured by CLEA Japan, Inc) from 10:00, and the food intake was measured over time after 1 hour, 2 hours, 3 hours, 6 hours, and 24 hours. The amount of the feed taken is expressed as the cumulative food intake (kcal) or the food intake at each time (kcal) (FIG. 1A). The cumulative food intake (kcal) also includes energy of administered GABA (3.95 kcal/g).

In order to examine the involvement of the vagus nerve which is a visceral sensory nerve, the food intake reducing effect by intragastric administration of GABA was examined using sensory nerve disorder model mice by subcutaneous administration of capsaicin or subdiaphragmatic vagotomized mice. The sensory nerve disorder model mice by subcutaneous administration of capsaicin were prepared as follows. 50 mg/kg of capsaicin (5 ml/kg, solution composition: 10% ethanol, 10% Tween 80, 80% physiological saline) was subcutaneously administered to C57BL/6J male mice under tribromoethanol (200 mg/kg, intraperitoneal administration (ip)) anesthesia, and after 2 days, 50 mg/kg of capsaicin was subcutaneously administered under similar anesthesia. Further, after 2 days, 10 mg/kg of capsaicin was intraperitoneally administered under no anesthesia. After a recovery period of 5 to 7 days, an experiment of food intake was performed. In sham operation and subdiaphragmatic vagotomy, surgery was performed on C57BL/6J male mice under tribromoethanol (200 mg/kg, ip) anesthesia. After the surgery, a liquid diet (milk for infants, 0.644 kcal/ml) was fed, and after a recovery period of about one week, an experiment of food intake was performed. All the mice were fasted overnight (16 hours) on the day before the experiment of food intake, then intragastrically administered a single dose of physiological saline or GABA (200 mg/kg) from 9:45, and fed at 10:00, and the food intake by free-feeding was measured over time. Capsaicin-treated mice were fed CE-2 feed, and sham-operated mice and subdiaphragmatic vagotomized mice were fed a liquid feed (FIG. 1B).

From the results of FIG. 1A, it was found that when an effective amount of a GABA solution (20 mg/kg or 200 mg/kg) was administered, the food intake within 2 hours from the start of diet after fasting was reduced as compared with the case where physiological saline was administered. In particular, the fasting food intake within 1 hour from the start of diet after fasting was significantly reduced, whereas the food intake after 2 hours from the start of eating was not always changed as compared with the case where physiological saline was administered. These data showed that although GABA induces the feeling of satiety in subjects, it is transient and can suppress binge eating on a fasting condition.

An ability to induce the transient satiety or an ability to suppress binge eating on a fasting condition by GABA confirmed in FIG. 1A was impaired by capsaicin treatment and afferent vagotomy ("SENSORY NERVE DISORDER MODEL MICE BY CAPSAICIN" and "SUBDIAPHRAGMATIC VAGOTOMIZED MICE" in FIG. 1B), but was similarly observed in sham-operated mice ("SHAM-OPERATED MICE" in FIG. 1B). This suggests that the vagal afferent nerves are involved in the ability to induce the transient satiety or the ability to suppress binge eating on a fasting condition by GABA.

Example 2: Enhanced Satiety Via Vagal Afferent Nerves by GABA Administration

Healthy C57BL/6J male mice or subcutaneously capsaicin-treated C57BL/6J mice were fasted for 16 hours (from 18:00 on the day before the experiment). Saline (40 ml/kg, po), GABA (200 mg/kg, po), EnsureH (40 ml/kg, po, 1.5 kcal/g) which is an enteral nutrient manufactured by Abbott Japan LLC, or EnsureH+GABA (GABA 200 mg/kg in Ensure, 40 ml/kg, po) were administered from 9:15. The mice were fed 30 minutes after administration, and freely fed. The result at −0.5 h showed the energy (kcal) of the forcibly administered solution. At 0.5 h or after, the cumulative food intake (kcal) of the forcibly administered solution and the feed taken was shown (FIG. 2).

Even if GABA was administered 30 minutes before eating, the eating behavior after the start of eating was not different from the case where physiological saline was administered 30 minutes before eating. On the other hand, as compared with the case where the nutrient was administered 30 minutes before eating, when the nutrient+GABA were administered 30 minutes before eating, the food intake within 1 hour after the start of eating was reduced, and in particular, the food intake within 30 minutes was significantly reduced ("HEALTHY MICE" in FIG. 2). This trend was not observed in capsaicin-treated mice ("SENSORY NERVE DISORDER MODEL MICE BY CAPSAICIN" in FIG. 2). This suggests that the ability to induce the transient satiety or the ability to suppress binge eating on a fasting condition by GABA requires administration of GABA in a state where the vagal afferent nerves are activated by the presence of nutrients.

Example 3: Influence of Aversion

C57BL/6J male mice reared in individual cages were given two bottles of water only for 2 hours from 10:00 to 12:00 for 5 days, whereby the mice were acclimated to the water restriction schedule. On day 6, a 0.15% saccharin solution was presented for 30 minutes, and thereafter, lithium chloride (3 mmol/kg) was intraperitoneally administered, whereby the mice were made to acquire an aversion to the taste of the saccharin solution (conditioning). In the same manner, a control group to which physiological saline (10 mL/kg) was intragastrically administered and a test group to which GABA (200 mg/kg) was intragastrically administered were prepared. On day 7 serving as a rest day, the above-described water restriction schedule was performed. On day 8 serving as a test day, two bottles of a 0.15% saccharin solution and water were simultaneously presented for 30 minutes, and the preference of the saccharin solution (saccharin intake/total intake of two bottles×100, %) was determined.

The results are shown in FIG. 3. From this result, it was shown that the ability to induce the transient satiety or the ability to suppress binge eating on a fasting condition by GABA is not caused by a change in eating behavior caused by aversion.

Example 4: Effect of Combined Administration of GABA and Nutrient

C57BL/6J male mice were acclimated to the environment and experimental work by preliminary rearing and handling for 1 week or more in individual cages. Various solutions were intragastrically administered at 10:00 to mice fasted for 16 hours from 18:00 on the day before the experiment, and at 30 minutes thereafter, perfusion fixation was performed with a Zamboni fixative solution containing 4% paraformaldehyde as a main component, and the nodose ganglion and the brain were extracted, respectively. They were post-fixed, and a frozen section specimen was prepared. Using this frozen section specimen, immunostaining of phosphorylated ERK1/2 (pERK1/2), which is a neural activation marker, was performed, and each organ section was photographed with a fluorescence microscope and analyzed.

FIG. 4 shows the results of intragastric administration of physiological saline (10 ml/kg, po) or GABA (200 mg/kg, po). In addition, FIG. 5 shows the results of intragastric administration of physiological saline (40 ml/kg, po), EnsureH (40 ml/kg, po), or EnsureH+GABA (200 mg/kg in EnsureH, 40 ml/kg, po).

These results confirmed that administration of GABA alone does not affect afferent vagal activity (FIG. 4), but significantly enhances afferent vagal activation by nutrient when GABA is administered together with the nutrient that activates vagal afferent nerves (FIGS. 5A and 5B).

Example 5: Effect on Blood GIP and Blood GLP-1

Healthy C57BL/6J male mice were fasted for 16 hours from 18:00 the day before the experiment. At 10:00, various solutions shown in the figure were intragastrically administered (40 ml/kg). Thirty minutes after administration, blood was collected from the portal vein under isoflurane anesthesia. An anticoagulant (heparin (final concentration 50

IU/ml)) and a peptide degradation inhibitor (aprotinin (final concentration 500 KIU/ml) and vildagliptin (final concentration 10 μM)) were added in advance to the sampling syringe. The collected blood was cooled and centrifuged and stored at −80° C. until the obtained plasma was analyzed. The total GIP concentration (A) and the total GLP-1 concentration (B) in the blood were analyzed using ELISA kits (EZGLP1T-36K and EZRMGIP-55K) manufactured by Millipore Corporation.

In the administration of GABA alone, there was no change in blood GIP and GLP-1 concentration. Although the liquid feed (EnsureH) increased blood GIP and GLP-1 concentration, the addition of GABA to the liquid food suppressed GIP concentration to about ⅓ and increased GLP-1 concentration approximately double. EnsureH is a liquid feed in which saccharides (sugar (sucrose)), lipids, and proteins are mixed, and among them, lipids are particularly potent GIP secretion promoters. In addition, casein and soybean protein contained in EnsureH are potent GLP-1 secretion promoters. Fructose, a constituent of sugar, is also a potent GLP-1 secretion promoter, and lipids are also known to slightly promote GLP-1.

From FIG. 6, it was shown that GABA can suppress blood GIP increase by nutrient and can increase blood GLP-1 increase by nutrient.

Example 6: Influence of GABA Administration on Food Intake in Humans

It was examined whether GABA administration also affects the food intake in humans. In 13 human subjects (25 to 43 years old, 5 males and 8 females), changes in the food intake in the presence or absence of GABA administration were confirmed in the following test outline.

Specifically, each subject was fasted from 21:00 on the day before the test, and subjective evaluation (satiety, hunger, appetite) was performed by the VAS questionnaire at 12:00 on the test day. Thereafter, a sample (placebo group: dextrin, GABA group: GABA 100 mg) was taken in together with 50 mL of water, and immediately after that, diet (lunch box) was taken. Immediately after diet, at 30 minutes, 60 minutes, and 120 minutes after diet, subjective evaluation (satiety, hunger, appetite) was performed again by the VAS questionnaire, and the remaining amount of a lunch box was photographed to calculate intake kcal.

Results

The changes in the feeling of satiety in the GABA group and the placebo group are shown in FIG. 7. As shown in FIG. 7, it was found that GABA intake significantly increases the feeling of satiety immediately after diet, and 30 minutes and 60 minutes after diet (the upper part of FIG. 7). Also in the area under the curve (AUC), a significant increase in the feeling of satiety could be confirmed by GABA intake (the lower part of FIG. 7).

In addition, the changes in appetite in the GABA group and the placebo group are shown in FIG. 8. It was found that GABA intake significantly reduced the appetite after diet. It is considered that unnecessary binge eating can be prevented by GABA intake.

Further, the average values of the calorie intake in the GABA group and the placebo group are shown in FIG. 9. As can also be seen from FIG. 9, the calorie intake showed a significantly low value by GABA intake. This is considered to be because the feeling of satiety was obtained even with a small calorie intake by GABA intake.

Example 7: Suppression of Glucose-Induced GIP Secretion

Healthy C57BL/6J male mice fasted for 16 hours (from 18:00 on the previous day to 10:00 on the test day) were orally administered saline (10 ml/kg), glucose (1 g/kg), or glucose+GABA (2, 20, 200 mg/kg). Fifteen minutes later, the mice were anesthetized, and blood was collected from the portal vein. Total GLP-1 and total GIP in plasma were measured by ELISA kit (n=6). The results are shown in FIG. 10. In the figure, a, b, and c each indicate that there is a significant difference ($p<0.01$, two-way ANOVA, by Tukey's test).

As shown in FIG. 10, it was found that glucose induces GIP secretion, whereas GABA suppresses this glucose-induced GIP secretion (left in FIG. 10). On the other hand, it was found that glucose does not affect GLP-1 secretion, and that the addition of GABA does not significantly enhance GLP-1 secretion (right in FIG. 10). Increasing the concentration of GABA did not enhance GLP-1 secretion. This indicates that GABA taken together with glucose does not significantly affect GLP-1 secretion.

Example 8: Influence of GABA Administration on Intake of Isomerized Sugar

Healthy C57BL/6J male mice fasted for about 16 hours (from 18:00 on the previous day to 9:45 on the test day) were orally administered saline (10 ml/kg po, n=8), glucose (1 g/kg po, n=10), fructose (1 g/kg po, n=8), or glucose+fructose (1 g/kg po each, n=8). Thereafter, the mice were fed at 10:00 on the test day, and the food intake by free-feeding was measured over time. As shown in FIG. 11, when fructose is taken alone, the food intake is suppressed as compared with the control group (saline), whereas when isomerized sugars (glucose+fructose) are taken, the food intake is similar to that of the control group (saline). That is, it is found that, when fructose is taken alone, the feeling of satiety is induced as compared with the control group (saline), whereas when glucose is further taken in addition to fructose, glucose inhibits the satiety inducing action by fructose, and the feeling of satiety induced by fructose is suppressed.

The effect of GABA on the inhibitory action on fructose-induced satiety by glucose was examined. Healthy C57BL/6J male mice fasted for about 16 hours (from 18:00 on the previous day to 9:45 on the test day) were orally administered saline (10 ml/kg po, n=6), glucose+fructose (1 g/kg po each, n=6), GABA (60 mg/kg po, n=6), or glucose+fructose (1 g/kg po, respectively)+GABA (60 mg/kg po) (n=6). Thereafter, the mice were fed at 10:00 on the test day, and the food intake by free-feeding was measured over time. As shown in FIG. 12, it is found that when isomerized sugars (glucose+fructose) and GABA are taken together, the food intake is suppressed as compared with the case where the control group (saline) or isomerized sugar is taken alone. That is, it is found that GABA releases the inhibition of the intake inhibitory action of fructose by glucose.

Example 9: Enhanced Fructose-Induced GLP-1 Secretion

Healthy C57BL/6J male mice fasted for 16 hours (from 18:00 on the previous day to 10:00 on the test day) were orally administered saline (10 ml/kg po, n=5), fructose (1 g/kg po, n=5), glucose+fructose (1 g/kg po each, n=5), GABA (60 mg/kg po, n=5), or glucose+fructose (1 g/kg po, respectively)+GABA (60 mg/kg po) (n=5). Thereafter, the mice were anesthetized, and blood was collected from the portal vein. Total GLP-1 and total GIP in plasma were measured by ELISA kit. The results are shown in FIG. 13. In the figure, a, b, and c each indicate that there is a significant difference ($p<0.01$, two-way ANOVA, by Tukey's test).

As shown in FIG. 13, it was found that fructose enhances GLP-1 secretion whereas GABA further enhances fructose-induced GLP-1 secretion (left in FIG. 13). In addition, it was found that the GLP-1 secretion action by fructose is suppressed by the addition of glucose (isomerized sugar) whereas the GLP-1 secretion is enhanced by further addition of GABA (left in FIG. 13). It was also found that isomerized sugar induces GIP secretion whereas GABA suppresses this isomerized sugar-induced GIP secretion (right in FIG. 13).

Example 10: Intake Inhibitory Action by Intake of GABA and Sucrose (Sugar)

Healthy C57BL/6J male mice fasted for about 16 hours (from 18:00 on the previous day to 9:45 on the test day) were orally administered saline (10 ml/kg po, n=5), sucrose (2 g/kg po, n=5), GABA (200 mg/kg po, n=5), or sucrose (2 g/kg po)+GABA (200 mg/kg po) (n=5). Thereafter, the mice were fed at 10:00 on the test day, and the food intake by free-feeding was measured over time. As shown in FIG. 14, it is found that although the satiety inducing action (intake inhibitory action) is not observed in the case where sucrose (sugar) is taken alone, the food intake is suppressed in the case where sucrose (sugar) and GABA are taken together as compared with the case where the control group (saline) or sucrose (sugar) is taken alone. That is, it is found that GABA significantly induces the feeling of satiety by being taken together with sucrose (sugar). This result is valuable because sugar is the most utilized sweetener.

NOTES

As described above, the preferred embodiments of the present disclosure have been used as examples of the present disclosure, but it is understood that the scope of the present disclosure should be construed only by the claims. It is understood that the patents, patent applications, and other documents cited herein should be incorporated herein by reference in their entireties as if specifically set forth herein. The present application claims priority to Japanese Patent Application No. 2021-215421 filed in the Japanese Patent Office on Dec. 29, 2021, the contents of which are incorporated herein by reference as if fully set forth herein in their entirety.

INDUSTRIAL APPLICABILITY

The composition of the present invention can provide a composition for inducing transient satiety and/or suppressing binge eating, containing GABA, also existing in nature, as an active ingredient, and thus is useful in the health promotion industry and the food field.

The invention claimed is:

1. A method for suppressing secretion of glucose-dependent insulinotropic polypeptide (GIP) in a subject; the method comprising administering γ-aminobutyric acid (GABA) to the subject.

2. The method according to claim 1, for promoting secretion of glucagon-like peptide-1 (GLP-1) in the subject.

3. The method according to claim 1, for inducing transient satiety and/or suppressing binge eating on a fasting condition in a subject by suppressing secretion of glucose-dependent insulinotropic polypeptide (GIP), promoting secretion of glucagon-like peptide-1 (GLP-1), and/or activating vagal afferent nerves in the subject.

4. The method according to claim 3, for inducing transient satiety in the subject.

5. The method according to claim 3, for suppressing binge eating on a fasting condition in the subject.

6. The method according to claim 1, wherein the secretion of GIP is isomerized sugar-induced.

7. The method according to claim 1, for suppressing GIP secretion caused by diet.

8. The method according to claim 2, wherein the secretion of GLP-1 is fructose-induced.

9. The method according to claim 2, for promoting GLP-1 secretion caused by diet.

10. The method according to claim 3, for achieving the induction or suppression by activating vagal afferent nerves.

11. The method according to claim 1, for enhancing diet-induced nerve activation of vagal afferent nerves in the subject.

12. The method according to claim 1, wherein the GABA is administered in combination with a component that activates vagal afferent nerves.

13. The method according to claim 12, wherein the component that activates vagal afferent nerves is included in a diet.

14. The method according to claim 12, wherein the component that activates vagal afferent nerves includes energy-producing nutrients, dietary fiber, polyphenols, sugar alcohols, and degradation products thereof.

15. The method according to claim 1, wherein the GABA is administered in combination with glucose and sucrose.

16. The method according to claim 1, wherein the GABA is administered orally.

17. The method according to claim 1, wherein the GABA is administered to the subject in an amount greater than or equal to about 100 mg/individual.

18. The method according to claim 1, wherein the GABA is administered to the subject in an amount greater than or equal to about 100 mg/individual once every about 3 hours or more.

19. The method according to claim 1, wherein the amount of food intake within about 2 hours from the start of diet is reduced in the subject administered with the GABA compared to a subject not administered with the GABA.

* * * * *